United States Patent [19]

Stembridge et al.

[11] Patent Number: 5,799,059

[45] Date of Patent: Aug. 25, 1998

[54] PHANTOM AND METHOD FOR ACCURACY AND REPEATABILITY TESTING OF POSITIONAL MECHANISMS OF COMPUTER ASSISTED TOMOGRAPHY AND MAGNETIC RESONANCE IMAGING SYSTEMS

[76] Inventors: James H. Stembridge, 250 Springtree Dr., Apartment C-2, Columbia, S.C. 29223; Chisum Man, 2441 E. 72nd St., Brooklyn, N.Y. 11234

[21] Appl. No.: 688,509

[22] Filed: Jul. 30, 1996

[51] Int. Cl.$^6$ .................................................. G01D 18/00
[52] U.S. Cl. ........................................ 378/207; 378/18
[58] Field of Search ................................... 378/207, 18

[56] References Cited

U.S. PATENT DOCUMENTS

| | | | |
|---|---|---|---|
| 3,714,428 | 1/1973 | Gasaway | 250/59 |
| 5,052,035 | 9/1991 | Krupnick | 378/163 |
| 5,216,700 | 6/1993 | Cherian | 378/163 |
| 5,239,569 | 8/1993 | Saleh | 378/163 |
| 5,299,253 | 3/1994 | Wessels | 378/163 |
| 5,368,030 | 11/1994 | Zinreich | 123/653.1 |
| 5,416,816 | 5/1995 | Wenstrup | 378/18 |
| 5,419,324 | 5/1995 | Dillow | 128/653.1 |
| 5,427,099 | 6/1995 | Adams | 128/653.1 |
| 5,480,439 | 1/1996 | Bisek | 623/16 |

OTHER PUBLICATIONS

Guide for Radiation/Quality Assurance Program—Computed Tomography Equipment, New York State Department of Health, Bureau of Environmental Radiation Protection, Sep. 10, 1992.

*Primary Examiner*—Craig E. Church
*Attorney, Agent, or Firm*—Alfred M. Walker

[57] ABSTRACT

A transparent measuring phantom apparatus and method facilitates rapid testing of the accuracy and repeatability of the scan position mechanisms of patient support table movements of computer assisted tomography (CAT) and magnetic resonance imaging (MRI) systems. The phantom includes clear transparent acrylic sections and radiopaque acrylic numerals which are all adhesively or solvent bonded into the phantom. The phantom includes an acrylic tube enclosing a base plate, a longitudinally extending slice location bar, a plurality of sequential position indicator numerals and operator position indicator numerals between a pair of end plates. The slice locator bar has an array of slice locator holes. In operation, the long axis of the phantom is aligned with the long axis of table movement that determines the slice location. The slice locator holes are drilled into the slice locator bar in a repeating pattern. Each line of holes includes a deep center hole and a plurality of grade marker holes of lessor depth on each side of the center hole. The grade marker holes are placed on an angle of about 70.5 degrees from the horizontal. An X-ray beam or MRI scan scans through the phantom at any desired location to determine the accuracy of the movement mechanisms of the patent support table relative to the plane of the X-ray beam or MRI scan.

12 Claims, 7 Drawing Sheets

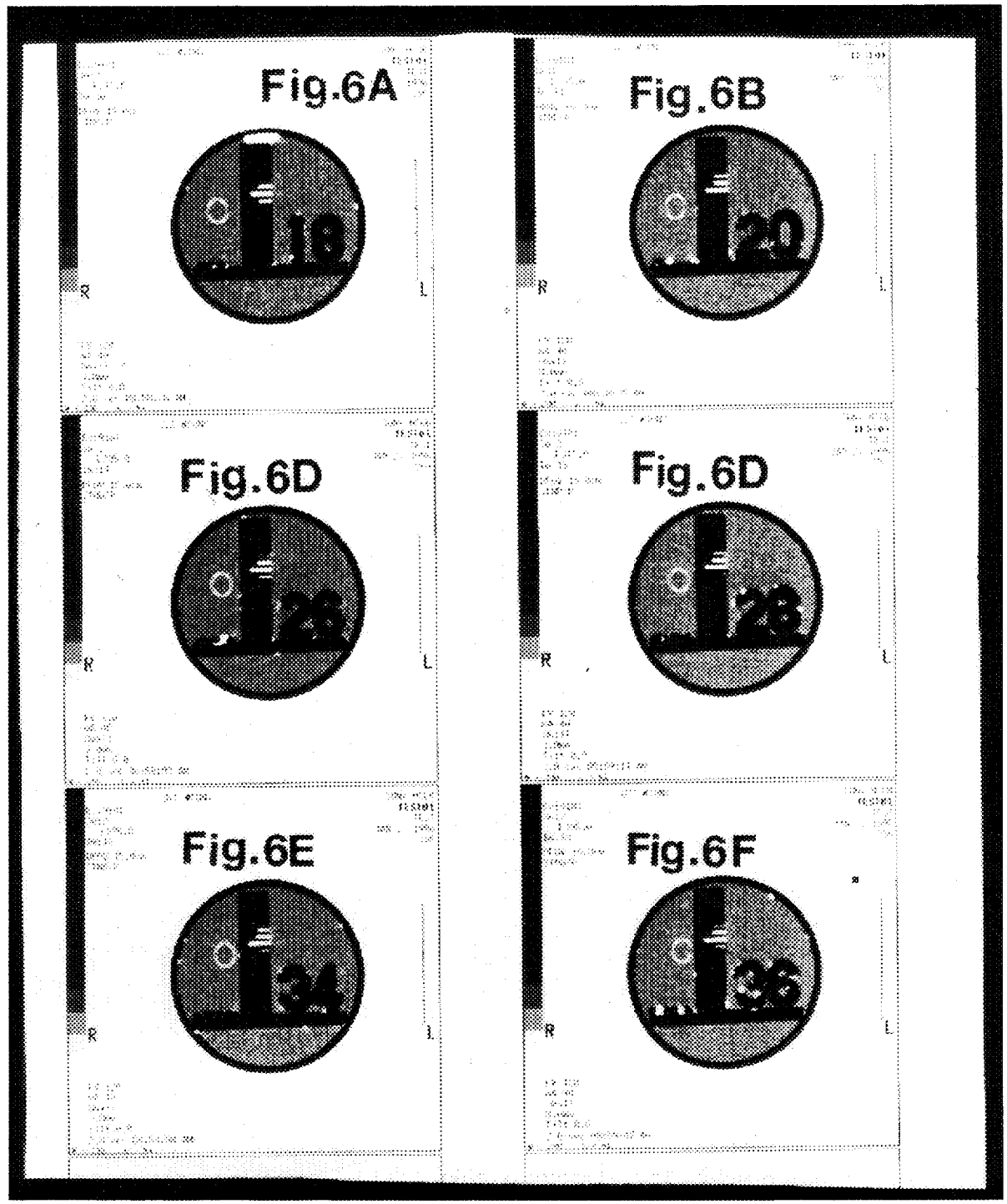

Procedure of Table Accuracy for CT:

1.) Align phantom on table with the orthogonal alignment lights.

2.) Landmark phantom at the "ZERO" position indicator.

3.) Take a axial scan of 3mm thickness using a minimal technique. For example: 120kVp, 4mA, 2 seconds scan time, 15cm FOV.

4.) Note the position of the graticule in the vertical bar, count the number of grades on both top and bottom of the center marker. The center marker is the longest grade.

5.) Take another scan 36cm from the first scan location, examine the image and count the number of grades above and below the center marker.

6.) The number of grades displaced should be the same on both images. If not, the number of grades greater or less than the one seen in the first image is the amount of displacement in millimeter.

Procedure of Repeatability for CT:

7.) Program the scanner to move the scan table back to zero position. Scan the phantom again with the same technique. Observe the image, the amount of displacement in grade should be zero. If not, this would indicate the slackness of table mechanical operation.

*For the MRI imager, use the same procedure as mentioned above with the following imaging technique: Spin Echo technique, single scan, TR = 350, TE = 15, NEX = 2, FOV = 16cm, automatic prescan.*

FIG. 7

PHANTOM AND METHOD FOR ACCURACY AND REPEATABILITY TESTING OF POSITIONAL MECHANISMS OF COMPUTER ASSISTED TOMOGRAPHY AND MAGNETIC RESONANCE IMAGING SYSTEMS

FIELD OF THE INVENTION

The present invention relates to an apparatus and method to facilitate rapid testing of the accuracy and repeatability of the scan position mechanisms (ie.- table movement) of computer assisted tomography (CAT) and magnetic resonance imaging (MRI) systems.

BACKGROUND OF THE INVENTION

Related art reveals several devices for marking, calibrating and aligning images from CAT and MRI systems. U.S. Pat. No. 5,299,253 of Wessels describes an alignment system and method to uniquely identify a cross-section of an imaged object to facilitate correlation of images. This is especially useful in identifying lesions near organs where a tumor may be obscured by an adjacent organ. It is however unrelated to the objective of this invention. U.S. Pat. No. 5,416,816 of Westrup describes a calibration template for computed radiography. It includes a variety of elements which simulate the X-ray absorption characteristics of various human body portions and organs. This device is useful for training radiologists and facilitates standardization of CAT image quality which is especially useful for remote analysis of transmitted radiographic digital data. This device is of little use in assessing accuracy of table movements however. U.S. Pat. No. 3,714,428 of Gasaway discloses a marker for radiology. A radiolucent member having stepped sloping edges with radio-opaque numerals is used to automatically record the height of the visible plane appearing on the film relative to a reference surface. The image of the numeral located closest to the plane is visible on the film while the remaining indicia are obscured. While the intent of Gasaway '428 is to include this device in the view of a patient radiograph, the physical aspects of the geometric placement of radio-dense numerals relative to X-ray scans bear some relationship to the present invention.

Other background art related to radiographic measurements in general include U.S. Pat. No. 5,052,035 of Krupnick, which discloses a grid template for producing a plurality of vertical and horizontal lines upon a radiographic film, to facilitate the location of a part of a human body within the grid template superimposed upon the radiographic images.

U.S. Pat. No. 5,216,700 of Cherian discloses a radiopaque marked tape measure attachable by an adhesive layer to a portion of a human body for correlating the location of a medical problem with a corresponding location upon an X-ray film.

U.S. Pat. No. 5,239,569 of Saleh describes a portable measuring rule placed adjacent to a portion of a human body, also for correlating the location of a medical problem with a corresponding location upon an X-ray film.

Other non-invasive radiographic film markers placed adjacent to a portion of a human body being subject to imaging include U.S. Pat. Nos. 5,368,030 of Zinreich, 5,419,324 of Dillow and 5,427,099 of Adams.

Moreover, an invasive radiographic marker is described in U.S. Pat. No. 5,480,439 of Bisek for a method of measuring bone density in the vicinity of a prosthetic implant having stored radiopaque reference markers therein.

However, these background art radiographic markers are of little use in periodically assessing the accuracy of the patient support table of medical imaging devices.

In relation thereto, preventive maintenance programs as well as state regulations dictate that CAT and MRI systems be tested for the accuracy and repeatability of their scan indexing mechanisms. Generally speaking, this involves the movements of a patient table relative to a fixed scanning subsystem.

For example, The "Guide for Radiation/Quality Assurance Program- Computed Tomography Equipment" from the New York State Department of Health- Bureau of Environmental Radiation Protection, stipulates that slice thickness, indexing accuracy, and position indicator accuracy be tested semi-annually.

To that end, the present invention facilitates the rapid evaluation of these parameters as well as repeatability on CAT and MRI equipment.

OBJECTIVES OF THE INVENTION

It is therefore an object of the present invention to provide a device for accurately measuring image slice thickness, indexing accuracy and position indicator accuracy of patient support tables and their associated medical imaging devices.

It is also an object of the present invention to provide an apparatus and method for rapid testing of the accuracy and repeatability of scan position mechanisms, such as patient support tables of medical imaging systems.

SUMMARY OF THE INVENTION

In keeping with these objects and others which may become apparent, the present invention is directed to a method of testing the accuracy and repeatability of the scan position mechanism of an imaging system, such as a Computerized Axial Tomography (CAT) scan or Magnetic Resonance Imaging (MRI) apparatus, wherein a scan position mechanism drives a support member, such as a movable table normally used to support a human subject, such as a medical patient, for imaging.

The method involves placing a measuring rule device, such as a phantom, on the patient support member, wherein the phantom includes a slice locator bar having a flat surface aligned with the direction of movement of the support member. The flat surface has drilled locator holes therein in a uniform repeating pattern consisting of a series of center holes of one depth and adjacent grade marker holes at a depth less than the center holes. The center and grade marker holes are uniformly spaced and a plurality of tangible indicia, such as specific sequentially aligned numerals, mark the center holes.

The method further includes taking a scan by the imaging system, such as the CAT scan or MRI apparatus, through the phantom and producing an initial image consisting of a plurality of lines corresponding to the larger center holes and the smaller grade marker holes, wherein the initial images includes a long line corresponding to a center hole and a shorter line corresponding to a grade marker hole and a specific numeral identifying a line corresponding to a center hole.

The patient support member is moved a predetermined finite distance, as indicated by the scan position mechanism, from the initial position of the patient support member and another scan is taken through the phantom by the imaging system, thereby producing an image consisting of a plurality of lines corresponding to the specific holes and a specific numeral corresponding to a center line on the image. The position of the specific lines and the specific numeral in the image are an accurate indication of the distance actually moved by the patient support member.

The selected finite distance is compared with the reading of the image indicating the distance actually moved by the patient support member, and any disparity represents an inaccuracy in the drive system for the patient support member.

The present invention also tests slackness in the drive mechanism of an imaging system. The same steps are done as before in measuring the distance traveled by the support member, except that instead of measuring the actual distance the support member travels, the support member is moved back the same predetermined finite distance first moved.

Then, another image is produced through the phantom showing the holes in the form of the long and short lines and the numeral identifying the center hole. The newly produced image is compared with that of the initial image, and the displacement of the lines indicate the degree to which there is slackness in the drive mechanism for the support member, such as a movable patient support table.

The aforementioned phantom used in calibrating and checking the accuracy of the drive mechanism of an imaging system is made of a hollow straight tube of transparent material, such as acrylic, wherein the tube is filled with air or a liquid, such as water or another liquid, wherein the liquid may have optionally a contrast rendering enhancer, such as acetic acid or copper sulfate.

The slice locator bar mounted in the tube has a flat, straight face extending the length of the tube. The tube includes a means for marking off distances on the flat face wherein the flat face has drilled therein specific locator holes in a uniform repeating pattern consisting the aforementioned series of center holes of one depth and the adjacent grade marker holes of lesser depths. The center and grade marker holes are preferably uniformly spaced, and the holes are capable of showing up on images produced by scans of the phantom tube by the imaging system as lines whose length correspond to the depths of the holes, wherein a long line represents a center hole and a shorter line representing a grade marker hole.

As noted before, the identifying indicia marker mounted in the tube for identifying each said center hole is an image of a numeral, which is displaced in a scan image adjacent its corresponding center hole.

Optionally, a duplicate set of numerals may be provided in the phantom for viewing by the operator of the imaging system, such as the CAT scan or MRI machine.

Moreover, preferably the slice indicator bar is mounted on and down the middle of one side of the base plate within the transparent tube. The base plate has on one side of the indicator bar the numerals facing in one direction for viewing by the operator of the CAT scan or MRI machine, and on the other side of the bar on the plate the numerals face in another direction, so that the numerals can be imaged.

BRIEF DESCRIPTION OF THE DRAWINGS

The present invention can best be understood in conjunction wit the accompanying drawings, in which:

FIGS. 5A, 5B and 5C are details of radiographic images taken in conjunction with the phantom as in FIG. 1, wherein:

FIG. 5A is an example of a slice of a typical "0" image;

FIG. 5B is an example of an aligned slice of a typical "36" image; and

FIG. 5C is an example of a misaligned slice of a typical "36" image;

FIGS. 6A-6F shows six actual positive print slice images taken in conjunction with the phantom as in FIG. 1;

FIG. 7 is a flow of procedures for accuracy and repeatability determinations, using the phantom as in FIG. 1;

DETAILED DESCRIPTION OF THE DRAWINGS

In the following description, dimensions and materials will be discussed that relate to the preferred embodiment. It is appreciated that deviations from these dimensions or the use of alternative materials will not alter the operation or intended use of this invention.

Figure 1:
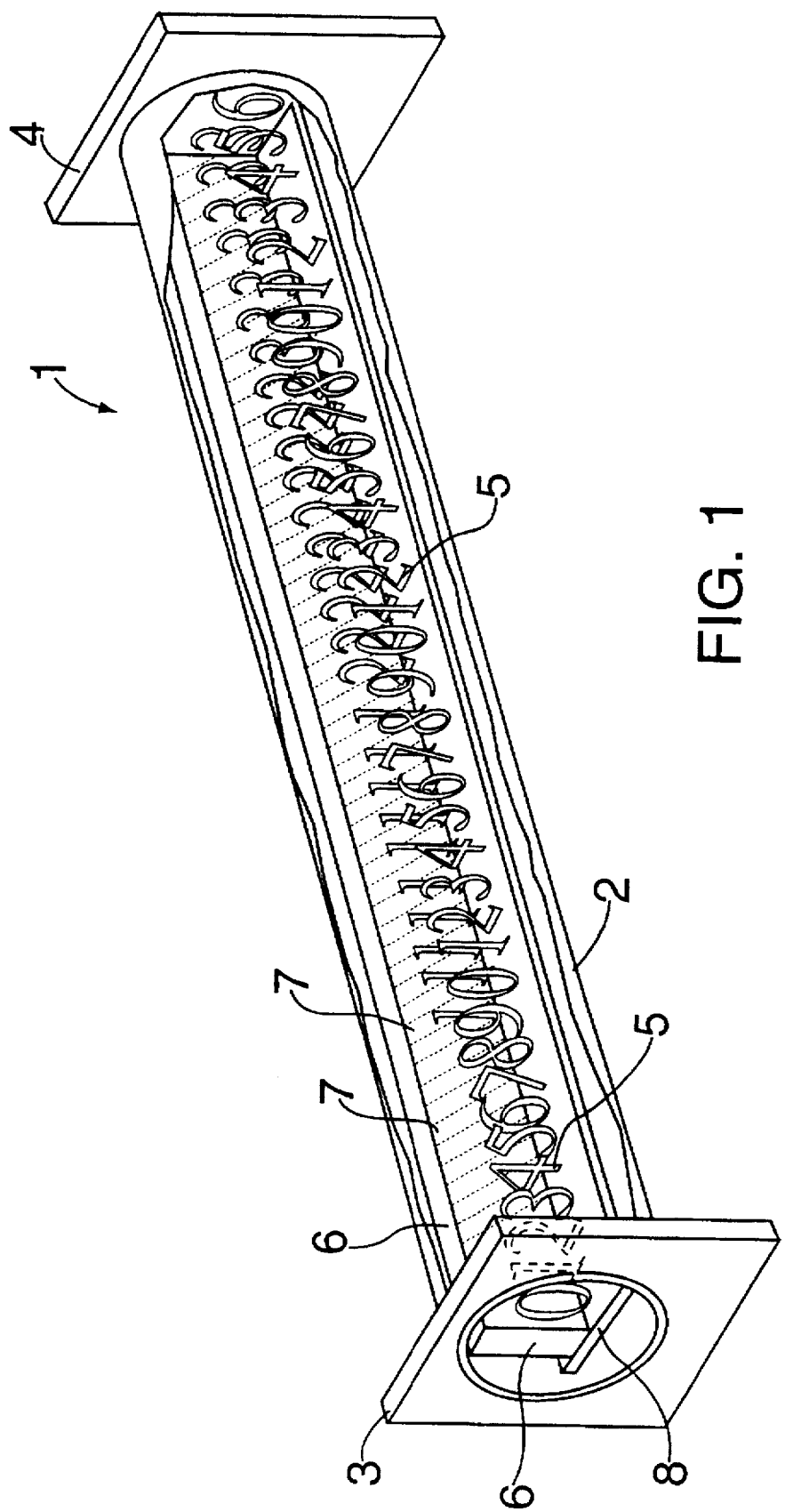
FIG. 1 is a perspective view of the transparent measuring rule phantom of the present invention.

The general construction of phantom 1 involves the use of clear transparent acrylic sections and white acrylic numerals which are all adhesively or solvent bonded into phantom 1 shown in FIG. 1.

Phantom 1 includes acrylic tube 2 enclosing base plate 8, slice location bar 6, upright position indicator numerals 5 and operator position indicator numerals (not shown in FIG. 1) between end plates 3 and 4. Slice locator bar 6 has an array of slice locator holes 7. In operation, the long axis of phantom 1 is aligned with the long axis of table movement of the patient support table, which determines the appropriate slice location.

Figure 2:
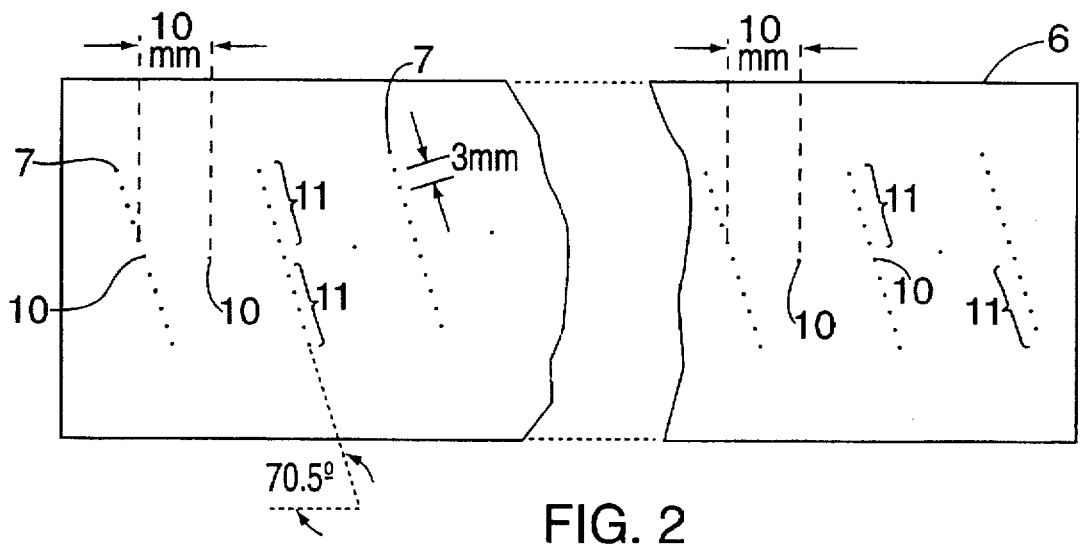
FIG. 2 is a side view of the slice location bar of the phantom as FIG. 1.

FIG. 2 is a side elevational view of slice locator bar 6. A series of blind slice locator holes 7 approximately 0.3 mm. in diameter is drilled into the bar in a repeating pattern. Each line of holes 7 includes center hole 10, which is preferably 8 mm. deep and preferably five grade marker holes 11 on each side, which grade marker holes 11 are 5 mm. deep and spaced 3 mm. apart on an angle of preferably about 70.5 degrees from the horizontal as shown. In FIG. 2, each line of holes 7 is spaced 20 mm. from the next line of holes 7, while intermediate center holes 10 are spaced centrally. An alternate embodiment includes of lines of holes 7 spaced every 10 mm. The horizontal spacing from the centers of adjacent holes in a line 7 is 1 mm.

Figure 3:
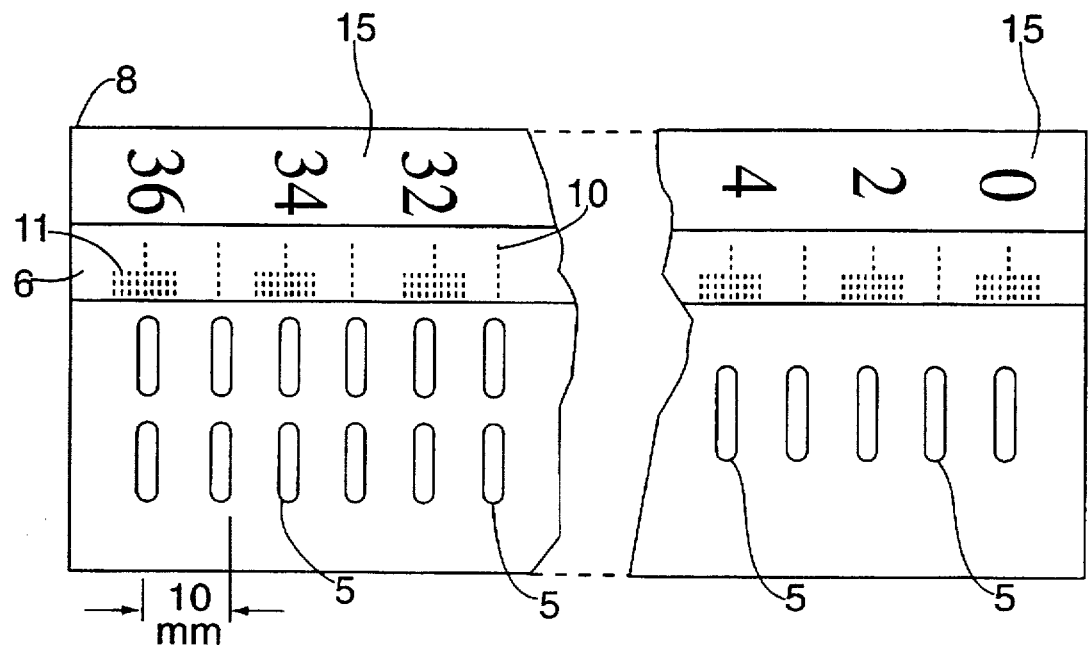
FIG. 3 is a top plan view of base plate with attachments of the phantom as in FIG. 1.

FIG. 3 is a top plan view of the internal subassembly within transparent tube 2, which tube 2 is made of a transparent material, such as acrylic plastic. Blind holes 10 and 11 can be seen as dotted lines in slice locator bar 6. Image locator numerals 15, which are operator position indicators, are approximately 15 mm. tall. In FIG. 3, top edges of upright position indicator numerals 5 are shown. Generally upright position indicator numerals are about 25 mm. tall, are spaced 10 mm. apart and are 3 mm. thick in cross section.

Figure 4:
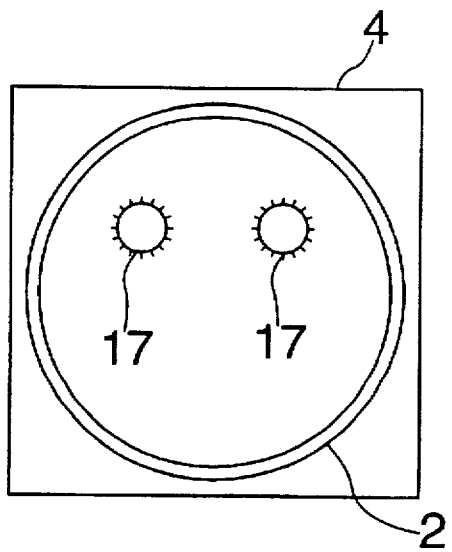
FIG. 4 is a front end view of the end plate of the phantom as in FIG. 1.

FIG. 4 shows end plate 4 of phantom 1 with two closable openings, such as entry holes closed by plugs 17, such as knurled acrylic plugs, which plugs 17 seal a hole in plate 4. Knurled plugs 17 can be removed to facilitate filling the interior of tube 2 above plate 8 with a liquid, such as water or other transparent image enhancer liquid that enhances contrast.

For CAT scan systems, it has been found that distilled water with a few drops of weak acetic acid, such as vinegar, as an algicide, enhances contrast as compared to an air filled enclosure. A copper sulfate solution is more effective for enhancing MRI contrast. Plugs 17 are screwed in to seal the enclosure of tube 2 after filling with the appropriate fluid.

Figure 5A:
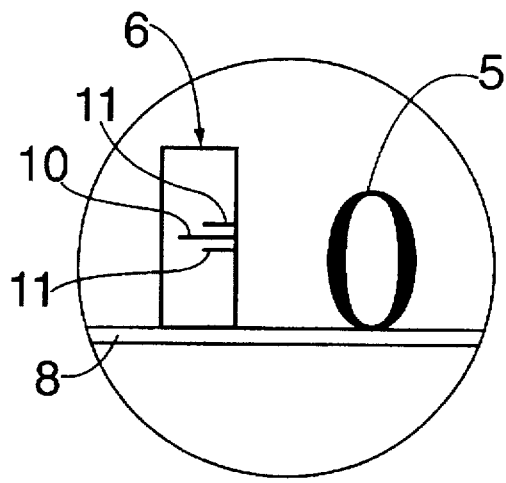
Figure 5B:
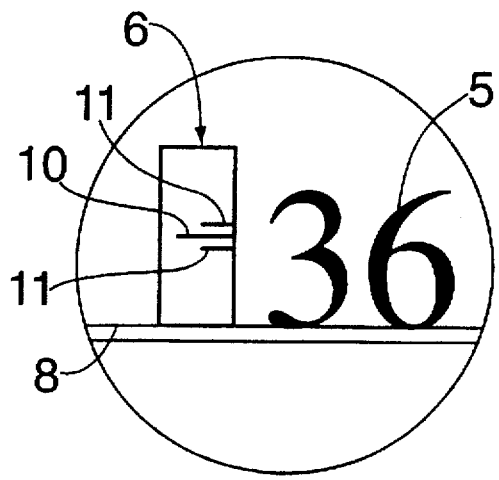
Figure 5C:
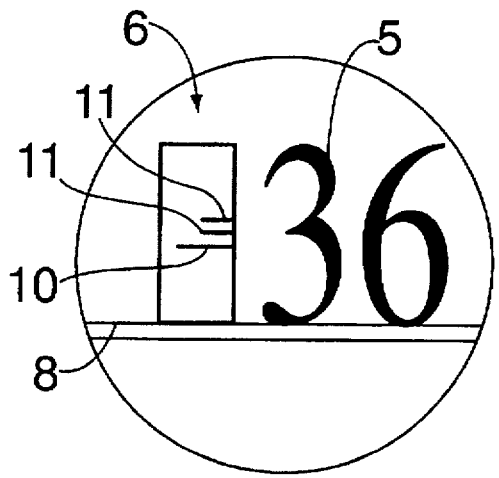

It can be appreciated that an X-ray beam or MRI scan of 3 mm thickness can scan through phantom 1 at any location. For example, FIGS. 5A, 5B and 5C show the details of the resulting radiographic images. In FIG. 5A, the radiographic beam intersecting a plane of tube 2 has scanned directly across the position indicating numeral 5, for "0", and the radiographic beam evenly illuminates center hole 10, and one grade marking 11 on either side in beam locator bar 6.

If the patient support table on which phantom 1 lies is then moved 36 cm by the mechanical adjustment provided therein to illuminate positional indicating numeral 5, for "36", then FIG. 5B shows a radiographic image indicating that the patient support table is perfectly aligned by virtue of the proper numeral, 36, and the fact that the same number and size of grade markers 11 on either side of center marker 10 show up in the same location and configuration as those shown for the "0" slice in FIG. 5A.

If a problem of movement accuracy of the patient support table exists by reason of machine movement slackness or other movement abnormalities, then use of phantom 1 will detect such movement abnormality. For example, FIG. 5C shows a 1 mm. inaccuracy, since the "36" slice shows an abnormal radiographic image of two grade markers 11 above the center marker 10, instead of one on each side, as in FIG. 5B.

FIGS. 6A–6F show positive prints of an actual radiographic negative from a CAT scan using the phantom 1. FIG. 6A shows slice "18" centrally aligned, and 6B shows slice "20" with a 1 mm. inaccuracy. FIG. 6C shows slice "26" almost centrally aligned since a shadow of a second grade marker is shown above the center marker. FIG. 6D shows a 1 mm. inaccuracy relative to slice "18" in slice "28". FIG. 6E shows a bit less than a 1 mm. deviation relative to slice "18" in slice "34", FIG. 6F shows a similar situation for slice "36".

FIG. 7 is a chart showing a six step procedure or method for table accuracy determination for CAT scan (or CT) equipment, along with a procedure for repeatability and setup for an MRI imager. The CT example setup of "120 kVp, 4 mA, 2 seconds scan time, 15 cm FOV" is typical for this procedure. "kvp" represents kilovolts potential. The 2 seconds scan time is for the entire rotation. "FOV" represents field of view. For the MRI imager, "TR=350" sets the repetition time to 350 ms. "TE=15" sets the echo time to 15 ms. after the pulse, and "NEX=2" sets the unit to 2 excitations or pulses.

Figure 8:
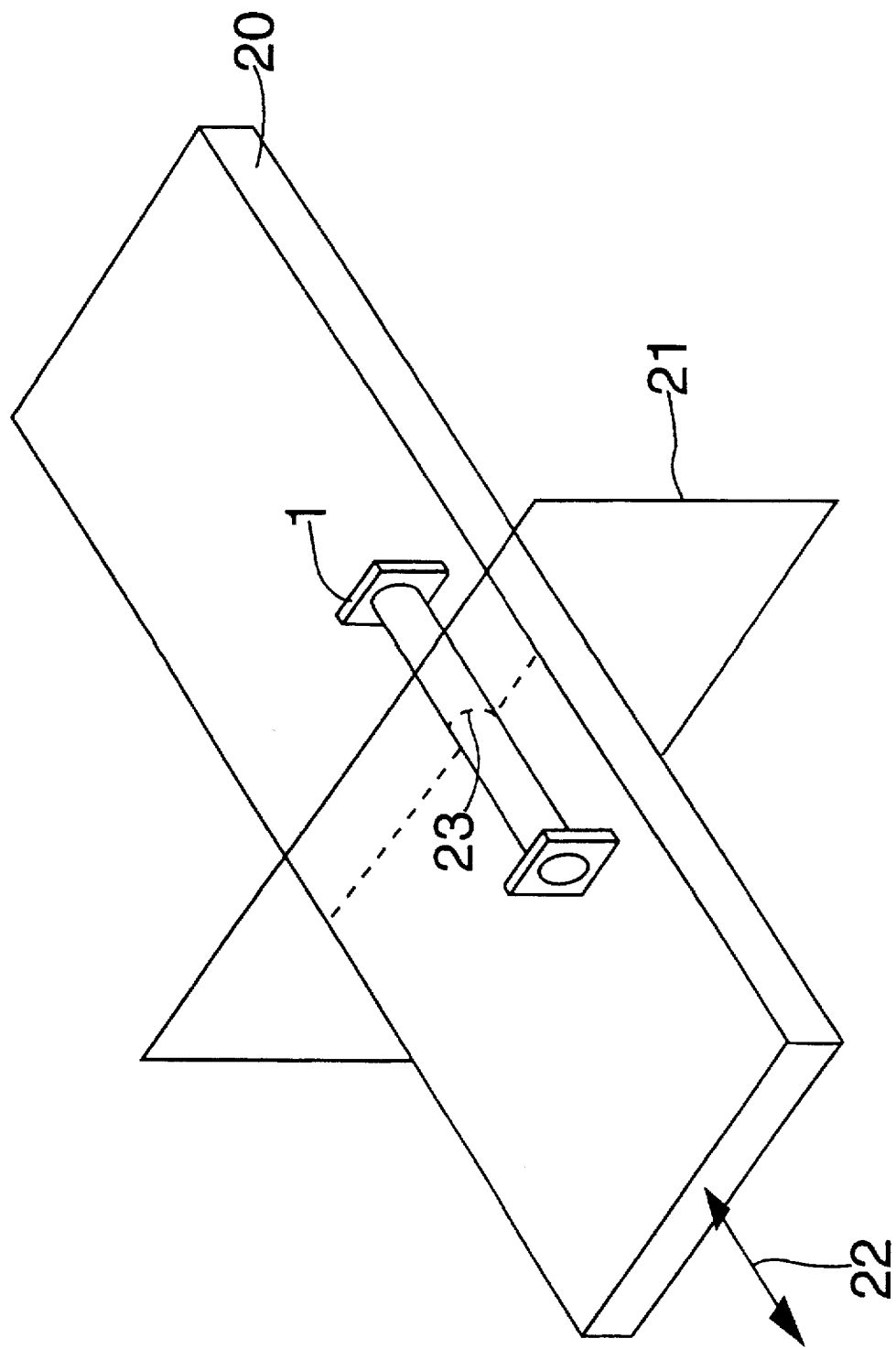
FIG. 8 is a perspective view of the phantom of the present invention, as in FIG. 1, shown in place upon a movable human body support member, wherein the phantom is intersected by a radiographic image plane; and, FIG. 9 is a schematic side elevational view of a CAT system in partial cross section, showing the phantom as in FIG. 1.

FIG. 8 shows a schematic perspective view of the relationship between the plantom 1 and patient support table 20 of an MRI or CAT system, phantom 1, as well as their relationship to imaging plane 21. In most systems, imaging plane 21 is fixed and patient support table 20 moves longitudinally, as indicated by arrow 22, so that different parts of the patient's anatomy can be "cut" by imaging plane 21.

It is important that phantom 1 be aligned with the long axis of patient support table 20. However, the lateral position of phantom 1 is not critical. Dotted line 23 indicates how the imaging plane 21 cuts across the phantom 1.

By examining both FIG. 8 and referring also to FIG. 3, it can be appreciated that imaging plane 21 cuts across slice location bar 6 and upright position indicating numerals 5. If the imaging plane width is 3 mm and it is positioned to cut through the center of an even upright numeral 5, imaging plane 21 also illuminates center hole 10 and one grade mark 11 on either side of center hole 10. When patient support table 20 is moved an even number of centimeters to another position, imaging plane 21 will cut across a different numeral 5. The accuracy of the movement of patient support table 20 can be gauged by viewing the pattern of grade markers 11 relative to the center hole 10 at the new position.

Figure 9:
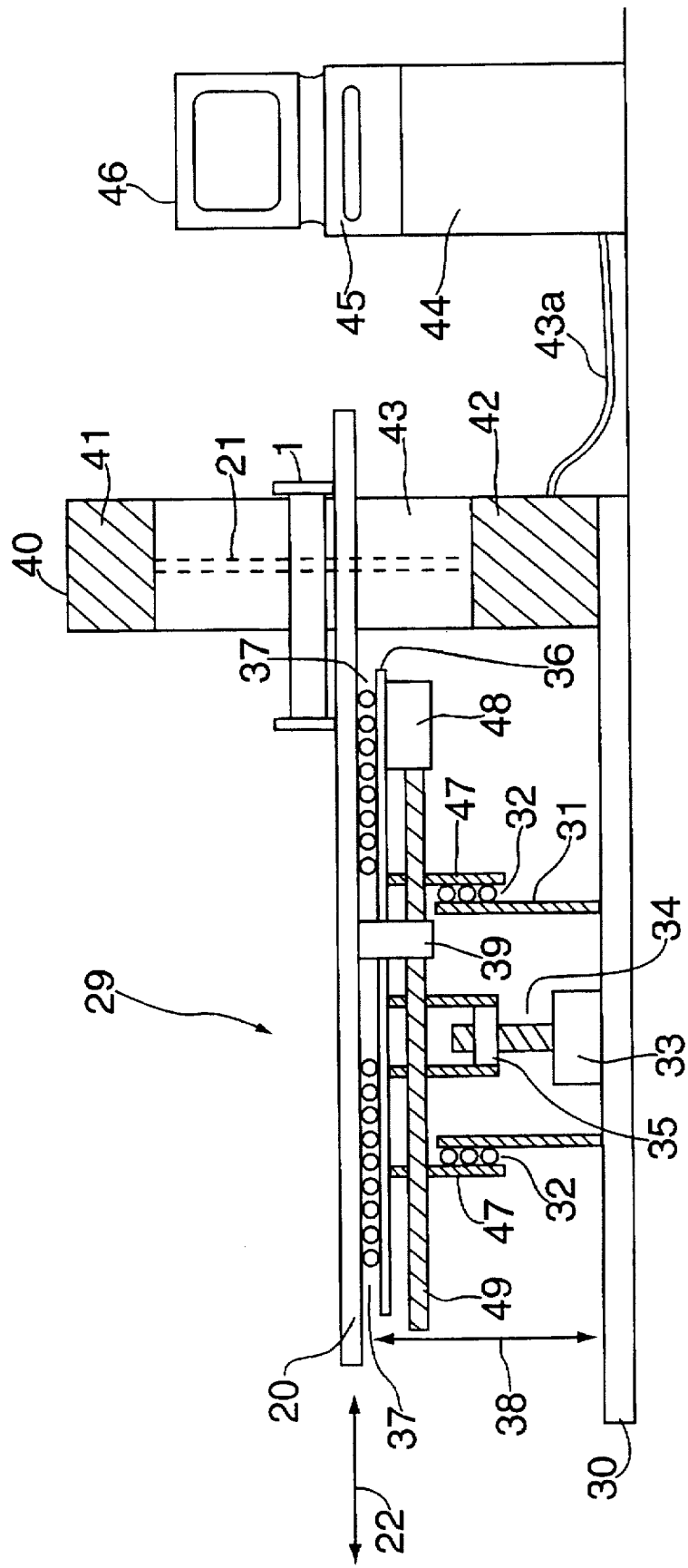

FIG. 9 is a schematic side view of a typical CAT system 29. Scanner 40 shown in cross section has X-ray detectors 41, which may be scintillation crystals, and an X-ray source 42. In the center of scanner 40 is an opening 43 through which the patient is moved. Phantom 1 is shown located through this opening.

In operation, both the X-ray detector array as well as the source rotate around the patient and as many as 90,000 readings are taken to create a single cross sectional image at the image plane 21. In computerized tomography, these readings are sent via cable 43a to be processed by computer 44, through algorithms which subtract or blur out extraneous images, to create a high definition cross sectional image. This image can be viewed as a color-enhanced picture on graphic terminal 46 or can be printed as a monochrome film radiograph on output device 45.

In an MRI system, the scanner 40 is replaced by a magnetic tunnel structure through which the patient is moved in steps. The imaging is based on nuclear magnetic resonance which results from the precessional properties of tiny magnetic moments of atomic nuclei. Hydrogen nuclei in tissue absorb stimulating electromagnetic radiation. Subsequent emissions by such protons can be detected and used to form high contrast images which are superior to CAT images in providing soft tissue contrast. Many such readings are required for a single MRI image, and the algorithms to construct such cross sectional images at image plane 21 are similar to those used in a CAT system.

Regardless of the imaging technique used, patient support table 20 is movable up and down in the directions indicated by arrow 38 and longitudinally in the direction indicated by arrow 22. Central pedestal 31, shown in cross section, is attached to base 30. Linear bearing elements 32 are used to provide support and guidance to outer pedestal sleeve 47 which is attached to table base 36. Motor 33 driving lead screw 34 can adjust the table 20 height by engagement with lead screw nut 35 which is rigidly attached to table base 36. Linear bearing members 37 guide patient support table 20 over table base 36 to which is attached motor 48. Motor 48 adjusts table 20 longitudinally through scanner aperature 43, through the action of driven lead screw 49 which engages lead screw nut 39. Lead screw nut 39 is rigidly attached to patient table 20 thereby moving it relative to table base 36 when motor 48 is energized, to move patient support table 20 into a proper position relative to phantom 1 and image plane 21 for measuring the accuracy of the movement of patient support table 20.

It is further noted that other modifications may be made to the present invention, without departing from the scope of the present invention, as noted in the appended claims.

We claim:

1. A method of testing the accuracy and repeatability of the scan position mechanism of an imaging system, said scan position mechanism driving a support means normally used to support a human subject for imaging, the method comprising the steps of:

a) placing a phantom on said support means, said phantom including a slice locator bar having a flat surface aligned with the direction of movement of said support means, said flat surface having drilled locator holes therein in a uniform repeating pattern consisting of a series of center holes of one depth and adjacent grade marker holes at a depth less than the center holes, said center and grade marker holes being uniformly spaced, and a plurality of numerals marking said center holes;

b) taking a scan by said imaging system through said phantom and producing an initial image consisting of a plurality of lines corresponding to said center and grade marker holes, a long line corresponding to a center hole and a shorter line corresponding to a grade marker hole and a numeral identifying a line corresponding to a center hole;

c) moving said support means a predetermined finite distance by said scan position mechanism from the initial position of said support member and taking another scan through said phantom by said imaging system, producing an image consisting of a plurality of lines corresponding to said holes and a numeral corresponding to a center line on said image, the position of said lines and numeral in said image being an accurate indication of the distance actually moved by said support means; and d) comparing the selected finite distance with the reading of the image indicating the distance actually moved, any disparity representing an inaccuracy in the drive system for said support means.

2. A method of testing the accuracy and repeatability of the scan position mechanism of an imaging system, said scan position mechanism driving a support means normally used for supporting a human subject for imaging, the method comprising the steps of:

a) placing a phantom on said support means, said phantom including a slice locator bar having a flat surface aligned with the direction of movement of said support means, said flat surface having drilled therein locator holes in a repeating pattern of uniform spacing consisting of a series of center holes of one depth and adjacent grade marker holes at a lesser depth, said center and a plurality of numerals marking said center holes, b) taking a scan by said imaging system through said phantom and producing an initial image consisting of a plurality of lines corresponding to said center and grade marker holes, a long line corresponding to a center hole and a shorter line corresponding to a grade marker hole and a numeral identifying a line corresponding to a center hole;

c) moving said support means a predetermined finite distance as indicated by said scan position mechanism from the initial position of said support means;

d) moving said support system back the same predetermined finite distance, e) producing another image through said phantom showing said holes in the form of long and short lines and a numeral identifying the center hole; and f) comparing the newly produced image with that of the initial image, the displacement of lines indicating the degree to which there is slackness in the drive mechanism for said support means.

3. A phantom for use in calibrating and checking the accuracy of the drive mechanism of a movable patient support table of an imaging system comprising:

a) a hollow straight tube of transparent material;

b) a slice locator bar mounted in said tube, said slice locator bar having a flat, straight face extending the length of said tube;

c) means for marking off distances on said flat face comprising said flat face having drilled therein locator holes in a uniform repeating pattern consisting of a series of center holes of one depth and adjacent grade marker holes of lesser depth, said center and grade marker holes being uniformly spaced, said holes capable of showing up on images produced by scans of said phantom by said imaging system as lines whose length correspond to the depths of said holes, a long line representing a center hole and a shorter line representing a grade marker hole; and d) identifying means mounted in said tube for identifying each said center hole with a numeral which is displayed in a scan image adjacent its corresponding center hole.

4. The phantom as described in claim 3 in which said identifying means include a duplicate set of numerals for viewing by the operator of the imaging system.

5. The phantom as described in claim 4 in which said slice indicator bar is mounted on and down the middle of one side of a base plate within said tube, said base plate having on one side of said indicator bar the numerals facing in one direction for viewing by said operator and on the other side of said bar on said plate the numerals facing in another direction for being imaged.

6. The phantom as described in claim 3 in which said tube is made of an acrylic.

7. The phantom as described in claim 3 in which said transparent material is a liquid.

8. The phantom as described in claim 3 in which said transparent material is a contrast rendering enhancer.

9. The phantom as in claim 8 in which said contrast rendering enhancer is a solution of water and acetic acid.

10. The phantom as in claim 8 in which said contrast rendering enhancer is a solution of water and copper sulfate.

11. The phantom as in claim 3 in which said hollow tube further comprises an end plate at each end thereof, at least one of said end plate having at least one closable opening therein.

12. The phantom as in claim 3 in which said phantom is aligned longitudinally with respect to the longitudinal axis of the movable patient support table.

* * * * *